(12) United States Patent
Lettieri

(10) Patent No.: US 10,952,823 B2
(45) Date of Patent: Mar. 23, 2021

(54) METHODOLOGY FOR THE REALIZATION OF AN ORTHODONTIC FUNCTIONAL DEVICE FOR THE TREATMENT OF FACIAL ASYMMETRIES

(71) Applicant: Clelia Lettieri, Naples (IT)

(72) Inventor: Clelia Lettieri, Naples (IT)

( * ) Notice: Subject to any disclaimer, the term of this patent is extended or adjusted under 35 U.S.C. 154(b) by 129 days.

(21) Appl. No.: 16/312,550

(22) PCT Filed: Jun. 26, 2017

(86) PCT No.: PCT/IB2017/000775
§ 371 (c)(1),
(2) Date: Dec. 21, 2018

(87) PCT Pub. No.: WO2018/002700
PCT Pub. Date: Jan. 4, 2018

(65) Prior Publication Data
US 2019/0209272 A1 Jul. 11, 2019

(51) Int. Cl.
| | | |
|---|---|---|
| *A61C 7/36* | (2006.01) | |
| *A61C 7/08* | (2006.01) | |
| *A61C 13/00* | (2006.01) | |
| *A61C 19/04* | (2006.01) | |
| *A61B 6/14* | (2006.01) | |
| *A61B 6/00* | (2006.01) | |

(52) U.S. Cl.
CPC ............... *A61C 7/36* (2013.01); *A61B 6/501* (2013.01); *A61C 7/08* (2013.01); *A61C 13/0013* (2013.01); *A61C 13/0019* (2013.01); *A61B 6/14* (2013.01); *A61C 19/04* (2013.01)

(58) Field of Classification Search
None
See application file for complete search history.

(56) References Cited

U.S. PATENT DOCUMENTS

| | | | |
|---|---|---|---|
| 8,711,178 B2* | 4/2014 | Cortes Provencio | ......................... A61B 5/1079 345/646 |
| 2015/0238280 A1* | 8/2015 | Wu | .......................... A61C 7/36 433/6 |

(Continued)

FOREIGN PATENT DOCUMENTS

| | | | | |
|---|---|---|---|---|
| WO | WO-2015132649 | * | 9/2015 | ............... A61C 7/10 |

*Primary Examiner* — Fan Zhang
(74) *Attorney, Agent, or Firm* — R. Ruschena Patent Agent, LLC

(57) ABSTRACT

The object of the present invention relates to a method for the production of an orthodontic functional device for the treatment of facial asymmetries. The present invention refers to the field of the technique comprising the manufacturing methods and the technique used to make orthodontic appliances, Specifically, it refers to a methodology that allows the artwork to be performed without making the operator dependent based on a cephalometric frontal path created by a computer so without ever contacting the patient with a functional orthodontic device for the treatment of facial asymmetries. Facial asymmetry is an alteration in skeletal growth that can be determined by several congenital or acquired factors that in patients with skeletal development in place. They exemplify the pathogenetic action by altering the functional harmonics of the entire stomatognathic apparatus.

2 Claims, 3 Drawing Sheets

(56) References Cited

U.S. PATENT DOCUMENTS

2016/0361139 A1* 12/2016 Webber .................... A61C 7/08
2017/0135850 A1*  5/2017 Veis ......................... A61C 7/10

* cited by examiner

TABLE 2

METHODOLOGY FOR THE REALIZATION OF AN ORTHODONTIC FUNCTIONAL DEVICE FOR THE TREATMENT OF FACIAL ASYMMETRIES

BACKGROUND OF THE INVENTION

1. Field of the Invention

The object of the present invention relates to a method for the production of an orthodontic orthopedic functional apparatus for the treatment of facial asymmetries. The present invention refers to the field of the technique comprising the manufacturing methods and the technique used to make orthodontic appliances. Specifically, it refers to a methodology that allows the artwork to be performed and without making the dependent operator, operation based on a cephalometric frontal tract generated by a computer so without ever coming into contact with the patient, a device functional orthodontic orthopedic for the treatment of facial asymmetries.

2. Brief Description of the Prior Art

Facial asymmetry is the alteration of skeletal growth which can be determined by several congenital or acquired factors that in skeletal development patients undergoing pathogenesis by altering the harmonic functionality of the whole stomatognathic apparatus. Among the unilateral development asymmetries there are congenital forms such us Hemifacial Microsomy, and shapes acquired as the outcome of condylar fractures that find the most pathological manifestation in cases where an ankylosis of TMJ is determined. The Hemifacial Microsomia manifests itself as a more or less acute structural and functional alteration of the maxilla facial complex. The goals of functional orthodontic therapy are to stimulate the functions of the stomatognathic system to perform vicarious functions for the absent structures and to stimulate a differential increase on both sides. Fractures of the mandibular condyles are a traumatic pathology often encountered in children following accidental falls and even in these cases the correct diagnosis and detection of anatomic damage will suggest the most appropriate orthodontic or surgical treatment to be performed. Facial symmetry break the equilibrium and symmetry of the line of the face and jaw. This problem reduce self-esteem, malnutrition can also cause mandible disabilities when bitten or masticated, in addition to digestion problems. To date, there are several orthodontic appliances to correct this disease. However, most of them act indirectly on the problem by inserting interlocking thickness on the healthy side and placing a guide on the other side in order to correct the disease. Using these devices involves very long therapy times, most of them also require the patient to keep them in their mouths all the time; these types of device require high patient collaboration so therapy cannot start at a very early age.

SUMMARY OF THE INVENTION

However, in the state of the art is an innovative functional orthodontic device for the treatment of facial asymmetries which aims to increase the mandible's verticality in order to correct asymmetry less invasively than current device such as the presented in the patent document with application number PCT/162015/000277. This device consists in a bite (18) which Cover the upper arch having a thickness corresponding to the front portion of the asymmetrical side which starts from the canine descending proportionally to the molar Table 2 FIG. 2 and FIG. 3. The bite (18) is provided with an anatomic shield (22) in the fornix to be applied on the asymmetrical side of the bite (18) and having the inclined occlusal surface of an angle equal to the mandibular asymmetry angle (16) having a border (20) from about one millimeter on the occlusal surface (19) of the asymmetrical portion of the canine to the molar at the vestibular cusp of the lower arch.

BRIEF DESCRIPTION OF THE DRAWINGS

Tab 1

Tab 2

Tab. 2

DETAILED DESCRIPTION OF THE PREFERRED EMBODIMENTS

Figure 1:
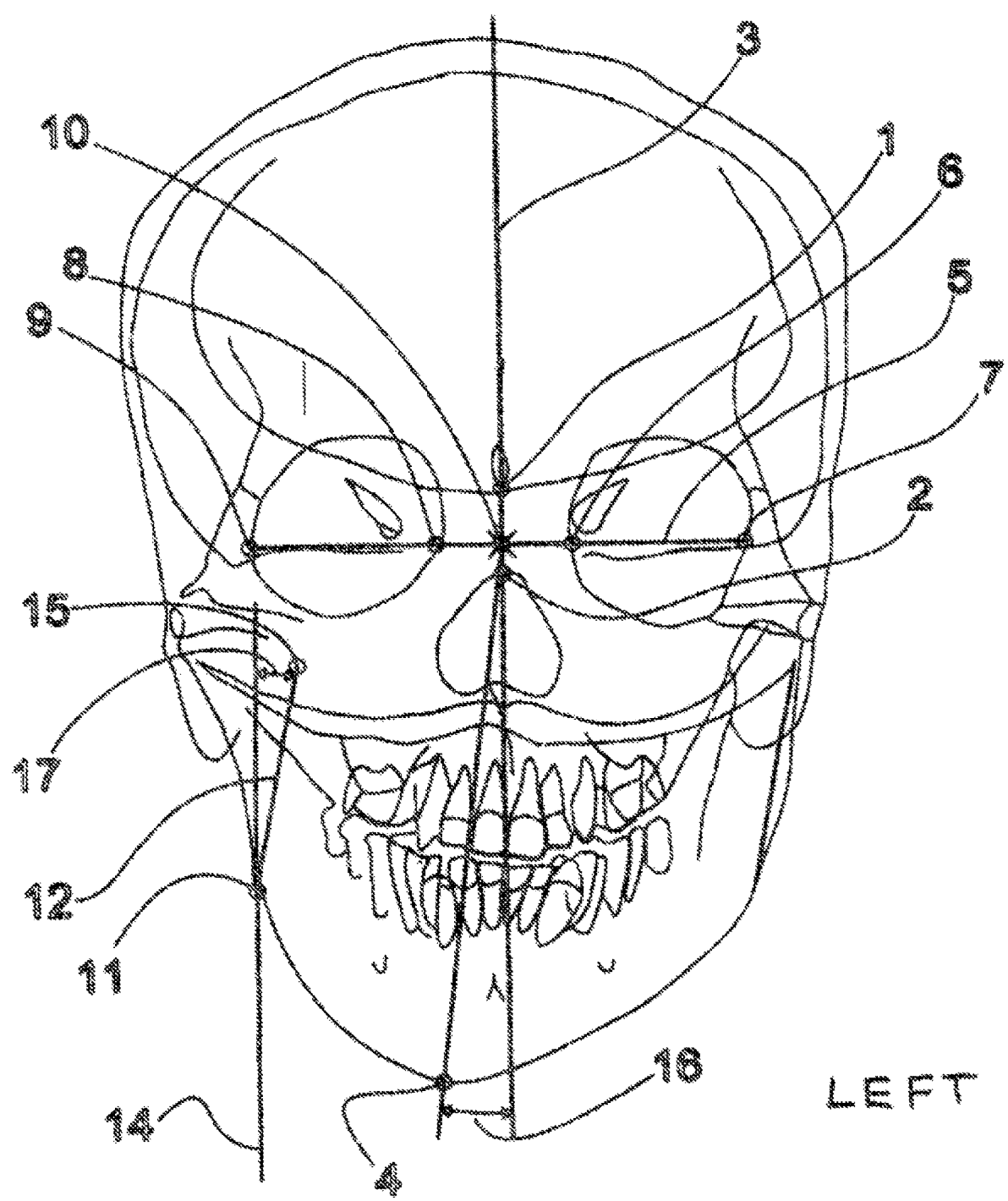
FIG. 1 is a view of the frontal cephalometric path generated by a computer on which reference points for the construction of the bite (18) and shield (22) are taken into account.
Figure 2:
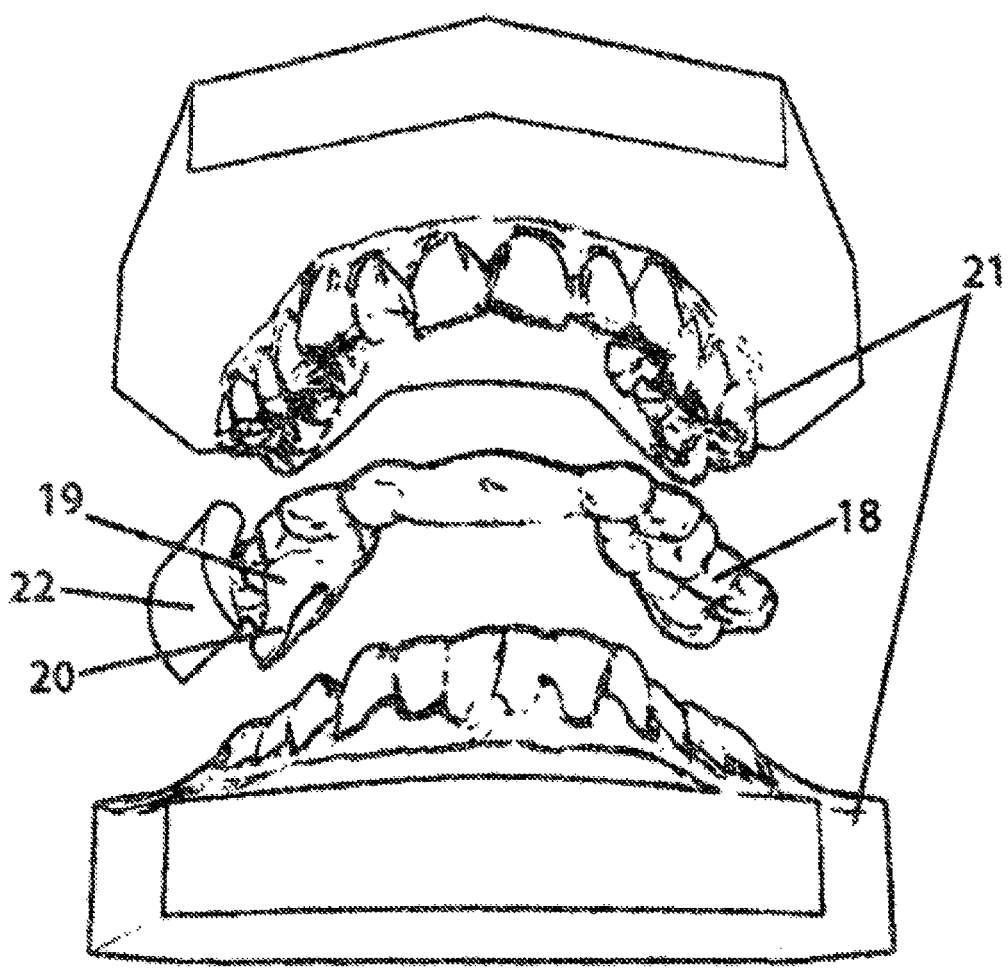
FIG. 2 is a prospective view of the patient's dental imprint (21) on which the bite is made (18)
Figure 3:
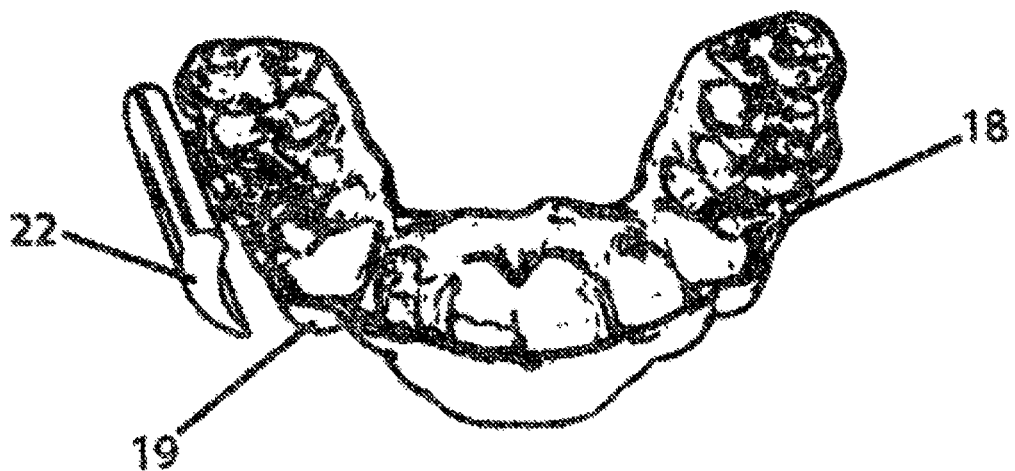
FIG. 3 is a prospective view of the orthodontic functional device for the treatment of facial asymmetries realized using the methodology presented by this patent application.
Figure 4:
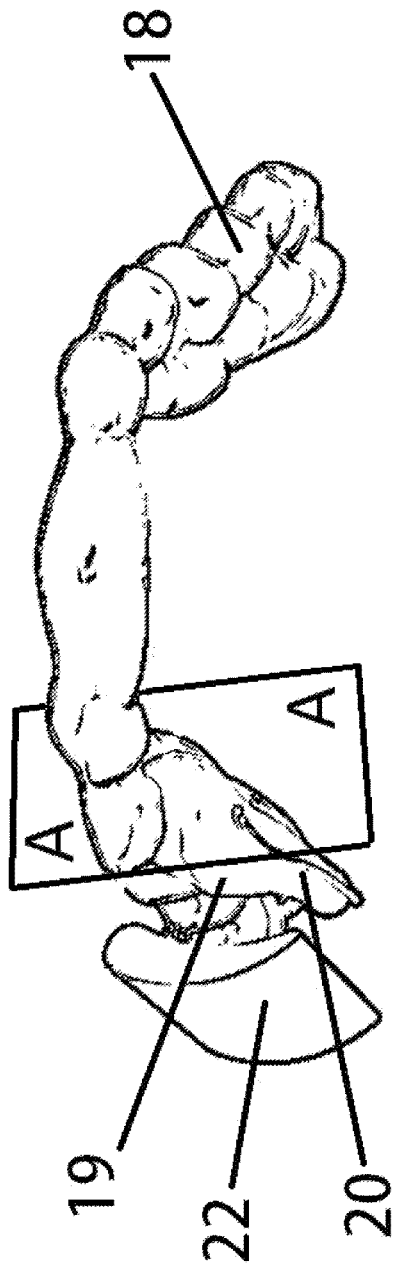
FIG. 4 shows a view of the bite, with the section plane A-A
Figure 5:
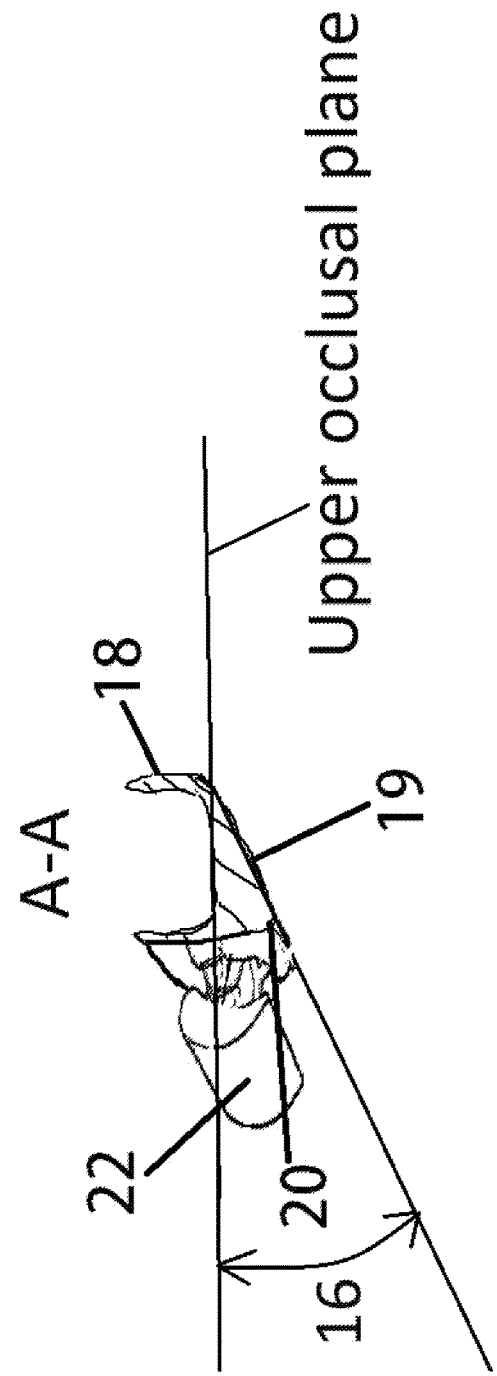
FIG. 5 shows a section view of the bite with the upper occlusal plane and the evidence of the angle (16) between the occluding surface with respect to the upper occlusal plane

The benefits of using this device are many. It is applied to upper arch, the application requires little work on the operator's dental chair, directly stimulates the mandible, the patient is not oblige'd to have his mouth closed, but only the search for contact during the swallowing, simplicity of the device which allows very early start of the functional therapy and prevents the structure of defect in the muscles, soft tissues etc., does not require a great collaboration of the patient, it can also be used only after dinner and during the night. The technical problem in the state of the art relates to the physical realization of this type of apparatus which has nowadays been empirically characterized, relying solely on the skill and experience of the technician who builds it on the basis of a dental cast (21) of the patient Table 2 FIG. 2 and FIG. 3. The purpose of the invention, object of the present invention, is therefore to provide a methodology that allows anyone to do this artwork starting from a cephalometric frontal tract generated by a computer, so without ever contacting the patient. According to another object, the object of the present invention is to provide a methodology for making a functional orthodontic device for the treatment of facial asymmetries in a fully automatic manner, for example, by utilizing 3D printing techniques. According to another purpose, the object of the present invention provides the orthodontic functional apparatus for the treatment of facial asymmetries even at a distance by simply transmitting the data relating to the cephalometric tract generated by a computer. The object of the present invention achieves the foregoing purpose as it is a method for the realization of an orthodontic, orthopedic functional apparatus for the treatment of facial asymmetries comprising the steps of:

Mapping of the vertical facial symmetry axis (3) by connecting the orbital midpoint (I) to the apex of the nasal septum (2) on a front cephalometric path generated by a computer Tab. 1 FIG. 1;

Plotting the bipupillar axis (5) by tracing a straight line that passes for the left lateral orbital point (7) for the left medial orbital point (6) for the right medial orbital point (8) and for the lateral orbital point right (9) Tab 1 FIG. 1;

Connect the intersection point (10) between the vertical facial asymmetry axis (3) and the bipupillar axis (5) with the anatomic point (4) Tab. 1 FIG. 1;

Measure the angle of mandibular asymmetry (16) that the axis of vertical facial asymmetry (3) forms with the passing line for the point of intersection (10) and the anatomic menton point (4) Tab. 1 FIG. 1;

making a bite (18) covering the upper arch with the occlusal surface inclinating an angle equal to the mandibular asymmetry angle (16) having a rib (20) of about one millimeter on the occlusal surface (19) of the portion of the asymmetric side from the canine to the molar at the vestibular cusps of the lower arch Tab. 2 FIG. 2 and FIG. 3;

draw a parallel line (14) to the vertical facial asymmetry axis (3) starting from the mandibular angle (11) on the asymmetrical side (12) Tab 1 FIG. 1;

measure the angle of asymmetry (17) that the parallel line (14) forms with the medial inclined mandibular branch asymmetric side (12) Tab. 1 FIG. 1;

realization of an anatomical shield (22) in the fornix to be placed on the asymmetrical side and with the inclination equal to the angle of condylar asymmetry (18) Tab 2 FIG. 3.

Therefore, it is possible to make the device in a state of art and without the risk of making mistakes related to the operator's limited experience.

Invaluable are the advantages of using this methodology that allows anyone and anywhere to create a functional orthodontic device for the treatment of facial asymmetries based on a frontal cephalometric tract generated by a computer without ever coming into contact with the patient. Anyone of the craft may better understand the invention by a detailed description of the drawing as follows.

The invention claimed is:

1. A methodology for the realization of a functional dental brace for the treatment of facial asymmetry, comprising the following steps:

tracking of vertical facial asymmetry axis (3) by joining an average orbital point (1) with the apex of a nasal septum (2) on a frontal cephalometric tracing, generated by a computer;

tracking of pupil axis (5) by drawing a straight line passing approximately through a left side orbital point (7), for a left medial orbital point (6), for a right medial orbital point (8) and for a right tide orbital point (9);

connecting a point of intersection (10) between the axis of vertical facial symmetry (3) and the pupil axis (5) with the anatomical menton point (4);

measuring the angle of mandibular asymmetry (16) that an axis of vertical facial asymmetry (3) forma with the straight line passing through the intersection point (10) and the anatomical menton point (4);

fabricating a bite (18) which covers a upper arch, having an occluding surface (19) inclined by an angle equal to the angle of mandibular asymmetry (16), having a rib (20) that measures about one millimeter, on an occluding surface (19) of the portion of the asymmetrical side from a canine up to a molar, in correspondence of a buccal cusps of a lower arch;

tracking a line (14) parallel to the axis of vertical facial symmetry (3) starting from the lower jaw (11) asymmetric side;

measuring an angle of condylar asymmetry (17) that the parallel line (14) forms with a mandibular inclined ramus medial asymmetric side (12);

fabricating an anatomical shield (22) In a fornix, to be affixed on the asymmetric side of the bite (18) inclined by the angle of condylar asymmetry (17).

2. The methodology for the realization of a functional dental brace for the treatment of facial asymmetry, according with claim 1, wherein said bite (18) and the shield (22) can be fabricated in a fully automatic way by a 3D printer or similar.

* * * * *